US009140674B2

United States Patent
DiSanzo et al.

(10) Patent No.: US 9,140,674 B2
(45) Date of Patent: Sep. 22, 2015

(54) METHOD FOR DETERMINING METHANOL CONTENT IN CRUDE OILS

(75) Inventors: Frank P. DiSanzo, Cherry Hill, NJ (US); Eric S. Shi, Singapore (SG); Masato Shibasaki, Chiba (JP); Shigeharu Yamamoto, Wakayama (JP); Hisao Morita, Wakayama (JP); Norio Takayama, Osaka (JP)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 252 days.

(21) Appl. No.: 13/523,251

(22) Filed: Jun. 14, 2012

(65) Prior Publication Data
US 2013/0061658 A1 Mar. 14, 2013

Related U.S. Application Data

(60) Provisional application No. 61/498,867, filed on Jun. 20, 2011.

(51) Int. Cl.
| | | |
|---|---|---|
| *G01N 33/22* | (2006.01) | |
| *G01N 30/02* | (2006.01) | |
| *G01N 30/16* | (2006.01) | |
| *G01N 33/28* | (2006.01) | |
| G01N 30/00 | (2006.01) | |
| G01N 30/06 | (2006.01) | |

(52) U.S. Cl.
CPC .............. *G01N 30/02* (2013.01); *G01N 30/16* (2013.01); *G01N 33/2823* (2013.01); *G01N 2030/009* (2013.01); *G01N 2030/062* (2013.01); *G01N 2030/065* (2013.01)

(58) Field of Classification Search
CPC ... G01N 30/00; G01N 33/0036; G01N 30/95; G01N 33/2823
See application file for complete search history.

(56) References Cited

PUBLICATIONS

PCT International Search Report issued Sep. 14, 2012 in corresponding PCT Application No. PCT/US2012/043104, 4 pp.
PCT Written Opinion issued Sep. 14, 2012 in corresponding PCT Application No. PCT/US2012/043104, 9 pp.
R.E. Pauls et al., "Gas and Liquid Chromatographic Analyses of Methanol, Ethanol, t-Butanol, and Methyl t-Butyl Ether in Gasoline", Journal of Chromatographic Science, vol. 19, Nov. 1981, pp. 558-561.
ASTM D7059-04, "Standard Test Method for Determination of Methanol in Crude Oils by Multidimensional Gas Chromatography", ASTM International Standard, US, vol. D7059-04, Jan. 1, 2004, pp. 1242-1256.

(Continued)

*Primary Examiner* — Laura Martin
*Assistant Examiner* — Alex Devito
(74) *Attorney, Agent, or Firm* — Andrew T. Ward; Glenn T. Barrett

(57) ABSTRACT

A test method for the determination of methanol in crude oils to levels as low as 0.5 ppm is disclosed. The method includes extracting methanol into a water phase from a test sample of the crude oil forming a test sample extract. The method further includes extracting methanol into a water phase from a reference sample of the crude oil forming a reference sample extract, wherein the reference sample having a predetermined amount of methanol added thereto. The method further includes measuring the methanol content in the test sample extract and the methanol content in the reference sample extract. The method also includes determining the methanol content of the crude oil based upon the methanol content in the test sample extract and the methanol content in the reference sample extract.

16 Claims, 5 Drawing Sheets

(56) References Cited

PUBLICATIONS

J.D. McCurry, "Using a New Gas Phase Micro-Fluidic Deans Switch for the 2-D GC Analysis of Trace Methanol in Crude Oil by ASTM Method D7059", Agilent Technologies, Nov. 3, 2004, pp. 1-6, XP-002682688.

A. Tippler, "Determination of Methanol in Crude Oils According to ASTM D7059-04 Using the Clarus 680 GC with S-Swafer Micro-Channel Flow Technology", Perkin-Elmer, May 7, 2010, pp. 1-6, XP-002682689.

Y. Zou et al., "Investigation of the Unique Selectivity and Stability of Agilent GS-OxyPLOT Columns", Agilent Technologies (Shanghai) Co. Ltd., Jun. 17, 2008, pp. 1-10, XP-002682690.

B. Mokhtari et al., "SPME-GC Determination of Methanol as a Hydrate Inhibitor in Crude Oil", Talanta, vol. 87, Dec. 15, 2011, pp. 118-125, XP 028114046.

B. Mokhtari et al., "Determination of Hydrate Inhibitor in Crude Oil by Nanoextraction-Gas Chromatography", Journal of Separation Science, (2012), vol. 35, pp. 79-85.

Z. Wang, "Chromatograph Qualitative and Quantitative", Chemical Industry Press, Jan. 31, 2000, pp. 172-173 (English translation provided).

Chinese Patent Application for Invention No. 201280024535.1, Office Action from the Patent Office of the Chinese State Intellectual Property Office (SIPO), dated Nov. 21, 2014, 37 pages.

HOW TO USE OASIS SEPPAK TO 'CLEAN' WATER EXTRACT

PRINCIPLE OF THE MEASUREMENT - STANDARD ADDITION METHOD
(1 ppm EXAMPLE)

- PREPARE CRUDE OIL SAMPLE AND 1 ppm - MeOH SPIKED CRUDE OIL SAMPLE
- EXTRACT MeOH FROM THE SAMPLE INTO WATER PHASE WITH EACH SAMPLES AND WATER BY EXTRACTION FUNNELS
- MEASURE MeOH CONTENTS OF THE EXTRACTED WATERS BY GAS CHROMATOGRAPH
- DETERMINE MeOH CONTENT IN THE CRUDE OIL BY THE CALCULATION FORMULA

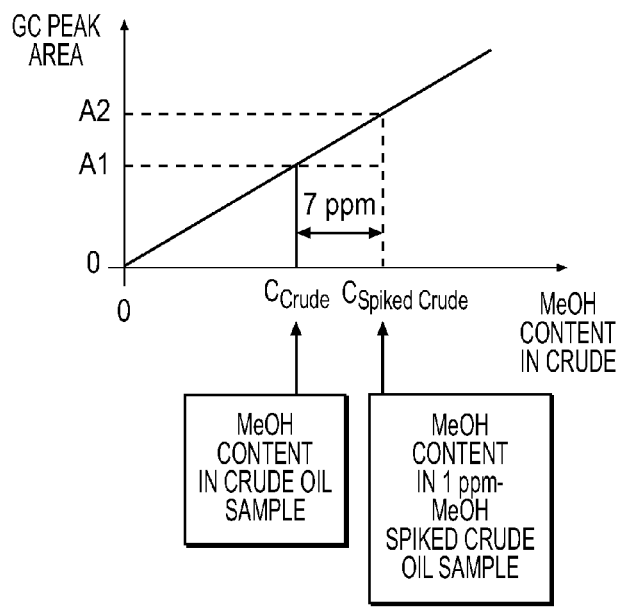

$C_{Crude} = A1 / (A2-A1)$

WHERE;

$C_{Crude}$: MeOH CONTENT IN CRUDE OIL

A1: GC PEAK AREA OF MeOH IN EXTRACTED WATER FROM CRUDE OIL SAMPLE

A2: GC PEAK AREA OF MeOH IN EXTRACTED WATER FROM 1 ppm-MeOH SPIKED CRUDE OIL SAMPLE

*FIG. 7*

METHOD FOR DETERMINING METHANOL CONTENT IN CRUDE OILS

CROSS REFERENCE TO RELATED APPLICATIONS

This application relates and claims priority to U.S. Provisional Patent Application No. 61/498,867, filed on Jun. 20, 2011.

FIELD

The presently disclosed subject matter relates to a testing methodology for the determination of methanol content in crude oils to levels as low as 0.5 ppm.

BACKGROUND

Methanol (MeOH) is commonly used in the production of crude oil. Methanol is used in deepwater production to prevent the formation of gas hydrates in crude oil exposed to cold temperatures when wells are shut in or when production rates are slowed. In particular, methanol is artificially introduced into the crude oil to prevent the formation of gas hydrates in, for example, deep sea crude production.

The presence of residual methanol in crude oil contaminates the crude oil, which can result in problems in subsequent refining operations when the crude oil is processed. Since methanol is miscible in water, it gets carried with the water in the crude oil to the refinery. The primary impact is on the refinery water treatment systems. When the refinery processes crude oil containing methanol in a desalter, the methanol is removed with the water and sent to the water treatment system where it can drastically upset the balance of the water treatment system. Specifically, when methanol is present, the bacteria that typically breakdowns other components prefers the methanol instead, leaving the other hydrocarbons and toxins untreated. This may produce environmental regulatory issues for the refinery resulting in fines and permit issues. The upset in the balance of the system may also lead to a catastrophic event that renders the water treatment system useless resulting in the need for major remediation efforts. As a result, refineries will typically opt to cut runs of methanol contaminated crude oil instead of risking environmental issues.

The determination of residual methanol content in crude oils is important to safeguard refineries against the processing of the contaminated crude oils that may be detrimental to the refinery causing shutdown of the water treatment plant due to methanol overload. As discussed above, high levels of methanol in the crude oil may jeopardize the refinery's water treatment systems. As such, crude oils with methanol contamination may not be processed in certain refineries. The level of contamination that impacts refining operations, however, may not be the same for all refineries. The equipment and systems at one refinery may be capable of processing crude oils with higher levels of methanol contamination when compared to another refinery. Some refineries have a very low tolerance for methanol contamination.

Currently, ASTM D7059-04 discloses a test method for determining methanol content in crude oil using multidimensional gas chromatography in the range of 15 to 900 ppm of methanol. ASTM D7079 uses gas chromatography with limited sample preparation, but complex hardware requirements. This method as specified by ASTM is only capable of measuring concentrations down to 5 ppm. There is a need for a testing methodology that permits the low-level detection of methanol in crude oil. Low-level methanol detection, for example, 5 ppm of methanol or less may expand a refinery's crude oil selection envelope. This may be especially useful for those refineries with capacity limitations in processing oxygenates containing crude or in discharging effluent water. Furthermore, the detection of low concentrations of methanol may assist refineries to quantifying the impact caused by methanol contamination of crude oil on their systems. As such, the refineries may develop practical guidance on (i) which crude oils are suitable for processing, and (ii) which crude oil should be accepted or rejected, which would allow the most economical deployments of crude across a group of refineries.

SUMMARY

A test method for the determination of methanol in crude oils to levels as low as 0.5 ppm is disclosed. The method includes extracting methanol into a water phase from a test sample of the crude oil forming a test sample extract. The method further includes extracting methanol into a water phase from a reference sample of the same crude oil forming a reference sample extract, wherein the reference sample having a predetermined amount of methanol added thereto. The method further includes measuring the methanol content in the test sample extract and the methanol content in the reference sample extract. The method also includes determining the methanol content of the crude oil based upon the methanol content in the test sample extract and the methanol content in the reference sample extract.

Extracting methanol into a water phase from either the test sample or the reference sample of the crude oil includes mixing a specified amount of the specific sample with a mixture of water and a solvent. The same quantity and ratio of water and solvent is used in connection with the extraction for both the test sample and the reference sample. During the extraction of the methanol, the crude oil is separated from the water and the methanol is contained in the water. In the event that the separation of the crude oil and the water unacceptable, an additional separation operation on the sample may be performed before analyzing the sample.

Both the test sample extract and the reference sample extract contain separated water and methanol. The measurement of the methanol content in both sample extracts includes analyzing at least a portion of the sample extract in a gas chromatograph. An additional clean-up operation on the sample extract may be performed in the event that the analysis of the sample extract indicates that the extract contains interferences. The cleaned-up sample extract may then be reanalyzed in the gas chromatograph.

The various features and the advantages of the disclosed subject matter are described herein and will become readily apparent to those skilled in the art from the following detailed description, including the accompanied figures as well as the claims.

BRIEF DESCRIPTION OF THE DRAWINGS

FIG. 7 is an example of a standard addition calculation according to the presently disclosed subject matter at the 1 ppm methanol level.

DETAILED DESCRIPTION

Figure 1:
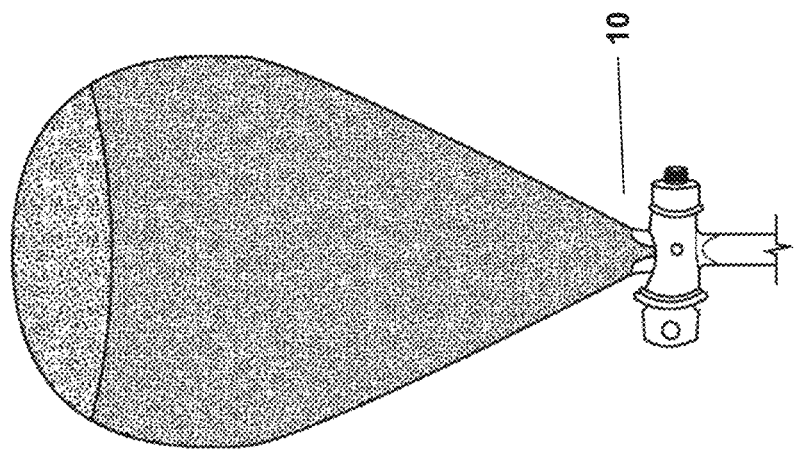
FIG. 1 is an illustration of a good or acceptable crude oil/water separation in accordance with the presently disclosed testing methodology.

The testing methodology in accordance with the presently disclosed subject matter will now be described in great detail. The method includes (i) the extraction of methanol from the crude oil into water, (ii) the purification of the extract, and (iii) the subsequent analysis of the extract using, for example, gas chromatography. The use of the extraction into water permits the determination of methanol concentrations at very low levels (i.e., below 5 ppm of methanol and preferably below 1 ppm). The present methodology, however, is not in tended to be used just for the determination of low levels of methanol in crude oils; rather concentrations up to and in excess of 1000 ppm may be effectively determined using the methodology.

In accordance with the presently disclosed subject matter, a sample of the crude oil to be tested is taken for analysis. The sample is preferably well-homogenized such that its composition is substantially the same throughout. The crude oil may be mixed or stirred such that the same is homogenized. It is contemplated that other means for creating a well-homogenized sampled may be employed. A test sample of the crude oil is taken from the well-homogenized sample. A reference sample of the crude oil is also taken from the well-homogenized sample.

The test sample is then treated to extract the methanol from the test sample. A mixture of water and a solvent is added to the test sample to facilitate separation of the crude oil and water. During this separation, the methanol contained within the crude oil is extracted into the water. The mixture may contain equal parts of water and solvent, but is not considered to be limited to such a ratio. Other ratios are contemplated provided the ratio of water to the solvent is sufficient to solubilize the oil such that the crude oil can be separated from the water. The solvent is preferably an organic solvent that will not precipitate out crude oil components (e.g., precipitate asphaltenes). Toluene has been found to be a very effective solvent. Xylenes are another effective solvent. Pentane, however, may not be an effective solvent because it will likely cause precipitation of asphaltenes and other organic components. The selection of appropriate solvent may also vary based upon the crude oil composition itself.

The mixture of water and solvent and the test sample may be combined in equal parts (e.g., 1 to 1 ratio). The presently disclosed testing methodology is not considered to be limited to such a ratio; rather, other ratios including both a greater proportion of test sample to the mixture and a lesser proportion of test sample to the mixture are contemplated provided such ratio permits the separation of the crude oil and water. The mixing of the water/solvent mixture and the test sample may be performed in a separating funnel 10, as shown, for example, in FIGS. 1 and 2. The combined mixture is then vigorously shaken or agitated and then permitted to stand. Over a predetermined period of time, the crude oil 11 separates from the water 12. The solvent remains in the crude oil. The methanol will migrate or separate from the crude oil into the water, whereby the methanol is extracted from the crude oil into the water. The predetermined period of time is sufficient such that the crude oil and water can separate. Thirty (30) minutes may be suitable for effecting this separation.

Figure 2:
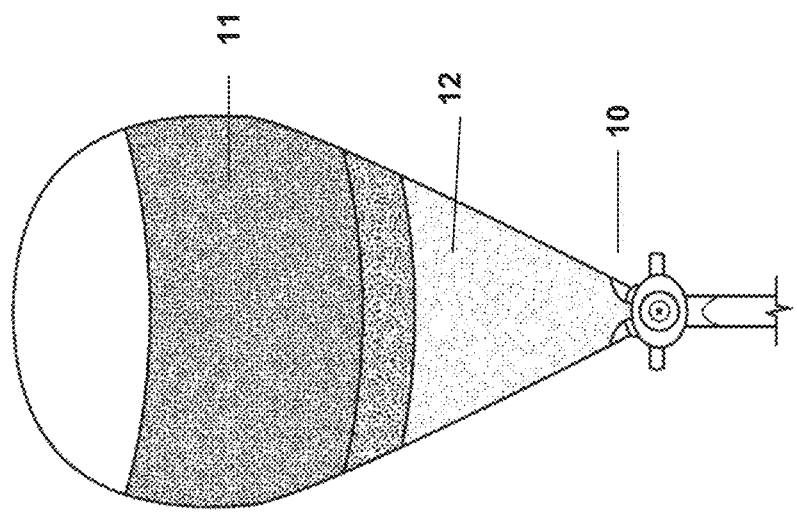
FIG. 2 is an illustration of a poor or unacceptable crude oil/water separation in accordance with the presently disclosed testing methodology.

An example of a good or acceptable separation between the crude oil and water is shown in FIG. 1. With such a separation, the water containing the extracted methanol can be removed from the funnel for further processing. The water is preferably filtered before further processing in order to remove any components that may impact the determination of the methanol content in the water. A paper filter may be suitable for performing such filtration. An example of a poor or unacceptable separation between the crude oil and water is shown in FIG. 2. With such a separation, additional processing is required before the water can be removed and filtered. It may be necessary to centrifuge the sample for a sufficient time in order to suitably separate the crude oil from the water. The sample may be separated into several centrifuge tubes for centrifuging. After centrifuging, the water containing the methanol may be removed and filtered in order to remove any components that may impact the determination of the methanol content in the water.

A test sample extract is then taken from the filtered water containing the methanol removed from the crude oil. The methanol content of the test sample extract is then measured. The methanol content of the test sample is preferably measured by injecting the test sample extract into a gas chromatograph (GC) equipped with capillary column and a flame ionization detector (FID) or other equivalent detection. The GC is equipped with a data handling system that is capable of accurately integrating the area of the measured methanol peak. The capillary column or equivalent is capable of separating methanol from other water soluble components in petroleum crude oil, e.g. DBWAX.

Figure 6:
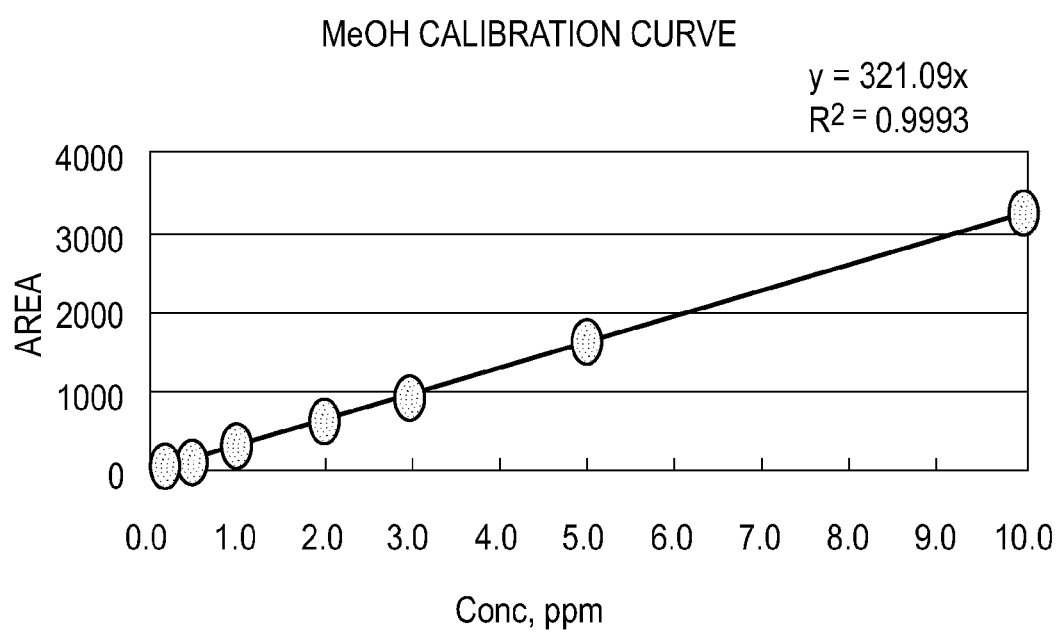
FIG. 6 is an illustration of the verification of the linearity of the GC hardware a series of methanol calibration standards prepared in water.

Prior to testing the test sample extract or the reference sample extract, described below, the linearity of the GC hardware is verified using a series of methanol calibration standards prepared in water. A verification of the linearity is illustrated in FIG. 6 for the low level determination of methanol. For higher concentrations of methanol, an appropriate linearity calibration is performed.

Figure 3:
FIG. 3 is an example of GC analysis of a sample spiked with 1 ppm of methanol showing the integrated methanol "peak" response.
Figure 4:
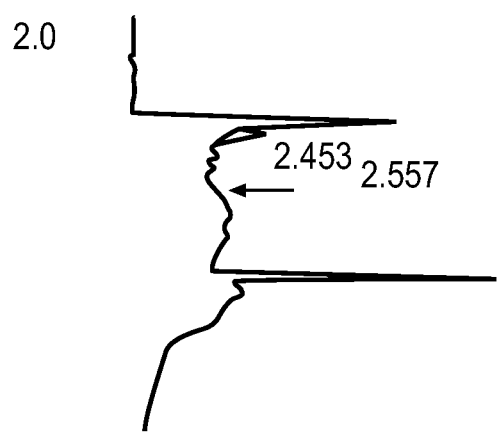
FIG. 4 is an example of GC analysis of a blank water or non-spiked sample.
Figure 5:
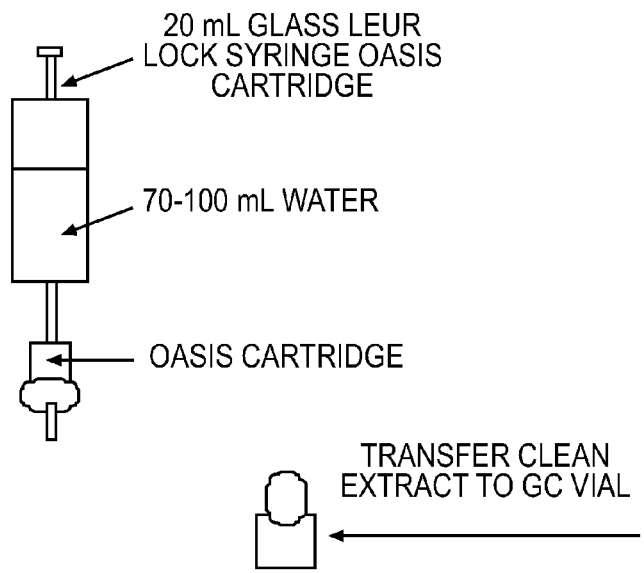
FIG. 5 is an illustration of the clean-up process for a sample for removing interfering components.
Figure 5:
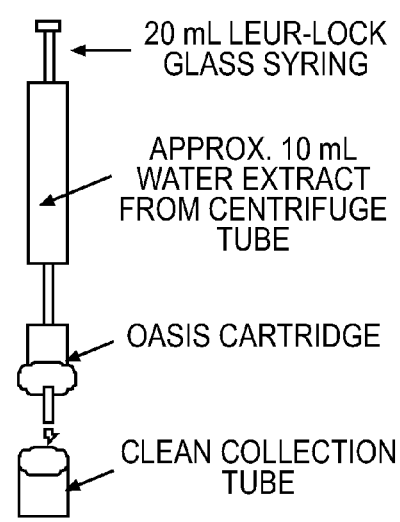

The GC measures the methanol peak. In some instances, the presence of other components in the test sample extract or the reference sample extract may interfere with the measurement of the methanol content. When interferences occur, it is necessary to perform an additional clean-up operation in order to remove these interferences such that any interfering peaks are removed. This is accomplished by further processing the sample extract. A portion of the sample extract is cleaned using, for example, an Oasis SepPak C18 cartridge or an equivalent device, which utilizes an affinity for the interfering components (e.g., hydrocarbons) to further separate out components. The clean up extraction cartridges, 'Oasis' C18 SepPaks, are available from Waters Corp (Milford, Mass., USA). The process for cleaning the sample extract is illustrated in FIG. 5. The cleaned sample water extract is then analyzed using the GC. A methanol peak area without interfering peaks is illustrated for the low methanol concentration, for example, in FIG. 3.

The reference sample of the crude oil is processed in the same manner as the test sample. Prior to processing, the reference sample is spiked with a predetermined quantity of methanol. For example, the reference sample may be spiked with 1 ppm of methanol. The presently disclosed subject matter is not intended to be limited to 1 ppm of methanol other volumes greater and less than 1 ppm are considered to be well within the scope of the present disclosure. The reference sample is then treated to extract the methanol from the reference sample in the same manner as the test sample, described above, using the same mixture of water and solvent at the same ratios or proportions. After separation and subsequent filtering, a reference sample extract is then taken from the filtered water containing the methanol removed from the crude oil. The methanol content of the reference sample extract is then measured in the same manner as the methanol content of the test sample extract. The clean-up process, described above, may also be used for the reference sample extract if the GC analysis illustrates the presence of any interferences.

From the measured methanol content of the test sample extract and the reference sample extract, the methanol content of the crude oil can be determined using standard addition methodology. The methanol content of the crude oil, for the 1 ppm example, is determined in accordance with the following relationship:

$$C_{crude} = (A1 \times C_{spike})/(A2 - A1)$$

where $C_{crude}$ is the methanol content of the crude oil;

$C_{spike}$ is the standard addition methanol content added into the reference sample of the crude oil (e.g., 1 ppm);

A1 is the GC peak area of methanol in the test sample extract; and

A2 is the GC peak area of methanol in the reference sample extract.

FIG. 7 illustrates an example for the standard addition calculation at 1 ppm methanol level. The methanol concentration is calculated from difference of the methanol peak area between two samples. The testing methodology is effective in monitoring methanol content within the 0.5 to 1.0 ppm range. This can be effective in permitting a refinery to select or deselect certain crude oils with unacceptable methanol content, which may produce a significant savings to the refinery associated with the avoidance of maintenance and other measures needed as a result of processing contaminated crude oils. It is estimated that such savings could exceed ten million dollars (US $ 10,000,000) on an annual basis for some refineries that are adversely effected by methanol content. For higher concentrations of methanol, the well established procedure of standard addition may be used employing multiple spikes.

The presently disclosed testing methodology is especially effective for several reasons including (i) its use of a special clean-up step to prevent interferences from other hydrocarbons, which is especially effective in analysis of very low concentrations at sub ppm level and (ii) the quantification by standard addition, which minimizes errors due to poor extraction as a result of matrix effects from differences in various crudes. Furthermore, the presently disclosed testing methodology uses relatively simple extraction and hardware typically used in GC.

While various embodiments of the disclosed subject matter are shown and described, it is to be understood that the invention is not limited thereto and may be variously embodied to practice within the scope of the following claims. It will be apparent to those skilled in the art that various changes may be made without departing from the spirit and scope of the invention as defined by the following claims.

The invention claimed is:

1. A method of determining methanol content in a crude oil, comprising:
    adding water to a test sample of the crude oil to extract methanol from the test sample into the water phase to form a test sample extract comprising water and extracted methanol;
    separating the test sample extract from the oil;
    adding water to a reference sample of the crude oil having a predetermined amount of methanol added thereto to extract methanol from the reference sample in the same manner as for the test sample to form a reference sample extract comprising water and extracted methanol;
    separating the reference sample extract from the oil;
    measuring the methanol content of the test sample extract;
    measuring the methanol content of the reference sample extract; and
    determining the methanol content of the crude oil based upon the methanol content of the test sample extract and the methanol content of the reference sample extract.

2. The method according to claim 1, further comprising:
    performing an additional separation operation on the test sample in the event that separation of the crude oil from the water is unacceptable.

3. The method according to claim 1, further comprising:
    performing an additional clean-up operation on the test sample extract in the event that the analysis of the test sample extract contains interferences.

4. The method according to claim 3, further comprising: reanalyzing at least a portion of the test sample extract in a gas chromatograph.

5. The method according to claim 1, wherein measuring the methanol content in the test sample extract includes analyzing at least a portion of the test sample extract in a gas chromatograph.

6. The method according to claim 5, further comprising:
    performing an additional clean-up operation on the test sample extract in the event that the analysis of the test sample extract contains interferences.

7. The method according to claim 6, further comprising: reanalyzing at least a portion of the test sample extract in the gas chromatograph.

8. The method according to claim 1, further comprising:
    performing an additional separation operation on the reference sample in the event that the separation of the crude oil from the water is unacceptable.

9. The method according to claim 1, further comprising:
    performing a clean-up operation on the reference sample extract in the event that the analysis of the reference sample extract contains interferences.

10. The method according to claim 9, further comprising: reanalyzing at least a portion of the reference sample extract in a gas chromatograph.

11. The method according to claim 1, wherein measuring the methanol content in the reference sample extract includes analyzing at least a portion of the reference sample extract in a gas chromatograph.

12. The method according to claim 11, further comprising:
    performing a clean-up operation on the reference sample extract in the event that the analysis of the reference sample extract contains interferences.

13. The method according to claim 12, further comprising: reanalyzing at least a portion of the test sample extract in the gas chromatograph.

14. The method according to claim 1, wherein the determined methanol content of the crude oil is accurate when the actual methanol content of the crude oil is less than 1000 ppm.

15. The method according to claim 14, wherein the determined methanol content of the crude oil is accurate when the actual methanol content of the crude oil is less than 5 ppm.

16. The method according to claim 15, wherein the determined methanol content of the crude oil is accurate when the actual methanol content of the crude oil is less than 1 ppm.

* * * * *